United States Patent
Bhalani et al.

(10) Patent No.: US 7,799,340 B2
(45) Date of Patent: *Sep. 21, 2010

(54) PHARMACEUTICAL COMPOSITIONS FOR LIPOPHILIC DRUGS

(75) Inventors: Vinayak T. Bhalani, Livingston, NJ (US); Satishchandra P. Patel, Livingston, NJ (US)

(73) Assignee: Watson Laboratories, Inc., Corona, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/686,555

(22) Filed: Mar. 15, 2007

(65) Prior Publication Data

US 2007/0259810 A1 Nov. 8, 2007

Related U.S. Application Data

(63) Continuation of application No. 10/207,146, filed on Jul. 30, 2002, which is a continuation of application No. 09/797,912, filed on Mar. 5, 2001, now Pat. No. 7,070,802, which is a continuation of application No. 09/196,353, filed on Nov. 19, 1998, now abandoned, which is a continuation-in-part of application No. 08/786,314, filed on Jan. 22, 1997, now Pat. No. 5,858,401.

(60) Provisional application No. 60/010,410, filed on Jan. 22, 1996.

(51) Int. Cl.
*A61K 9/66* (2006.01)
*A61K 9/48* (2006.01)
*A61K 9/64* (2006.01)

(52) U.S. Cl. .................. 424/455; 424/451; 424/452; 424/456; 514/11; 514/937; 514/938

(58) Field of Classification Search .......... None
See application file for complete search history.

(56) References Cited

U.S. PATENT DOCUMENTS

| | | | |
|---|---|---|---|
| 2,870,062 A | 1/1959 | Stanley et al. |
| 4,388,307 A | 6/1983 | Cavanak |
| 4,428,927 A | 1/1984 | Ebert et al. |
| 4,649,047 A | 3/1987 | Kaswan |
| 4,711,902 A | 12/1987 | Serno |
| 4,719,239 A | 1/1988 | Muller et al. |
| 4,722,941 A | 2/1988 | Eckert et al. |
| 4,722,999 A | 2/1988 | Handschumacher et al. |
| 4,727,109 A | 2/1988 | Schmidt et al. |
| 4,792,449 A | 12/1988 | Ausman et al. |
| 4,794,000 A | 12/1988 | Ecanow |
| 4,795,643 A | 1/1989 | Seth |
| 4,839,342 A | 6/1989 | Kaswan |
| 4,888,239 A | 12/1989 | Brox |
| 4,914,188 A | 4/1990 | Dumont et al. |
| 4,935,243 A | 6/1990 | Borkan et al. |
| 4,963,362 A | 10/1990 | Rahman et al. |
| 4,963,367 A | 10/1990 | Ecanow |
| 4,990,337 A | 2/1991 | Kurihara et al. |
| 4,996,193 A | 2/1991 | Hewitt et al. |
| 5,047,396 A | 9/1991 | Orban et al. |
| 5,047,512 A | 9/1991 | Handschumacher et al. |
| 5,051,402 A | 9/1991 | Kurihara et al. |
| 5,098,606 A | 3/1992 | Nakajima et al. |
| 5,116,816 A | 5/1992 | Dreyfuss et al. |
| 5,118,493 A | 6/1992 | Kelley et al. |
| 5,120,710 A | 6/1992 | Liedtke |
| 5,154,930 A | 10/1992 | Popescu et al. |
| 5,190,748 A | 3/1993 | Bachynsky et al. |
| 5,206,219 A | 4/1993 | Desai |
| 5,294,604 A | 3/1994 | Nussenblatt et al. |
| 5,314,685 A | 5/1994 | Tyle et al. |
| 5,342,625 A | 8/1994 | Hauer et al. |
| 5,376,381 A | 12/1994 | Weiner et al. |
| 5,389,382 A | 2/1995 | List et al. |
| 5,411,952 A | 5/1995 | Kaswan |
| 5,431,916 A | 7/1995 | White |
| 5,444,041 A | 8/1995 | Owen et al. |
| 5,474,979 A | 12/1995 | Ding et al. |
| 5,478,860 A | 12/1995 | Wheeler et al. |
| 5,504,068 A | 4/1996 | Komiya et al. |

(Continued)

FOREIGN PATENT DOCUMENTS

CA 2072509 12/1992

(Continued)

OTHER PUBLICATIONS

Product Information Partial glycerides; for Imwitor® and Softigen®, Hüls AG, revision 26.13.063e/04.97.

(Continued)

*Primary Examiner*—S. Tran
(74) *Attorney, Agent, or Firm*—Merchant & Gould PC

(57) ABSTRACT

Stable solutions of lipophilic drugs, such as cyclosporin, forming a polar lipid self-emulsifying drug delivery system. The solutions can include lipophilic drugs, such as cyclosporin, dissolved in a polar lipid, such as having a $C_6$-$C_{12}$ fatty acid monoglyceride content of at least about 50%, surfactants and triglycerides. The composition forms a fine emulsion on exposure to water. The encapsulated dosage form of this composition needs neither a hydrophilic component nor air-tight blister packaging, and is particularly suitable for oral administration.

21 Claims, No Drawings

U.S. PATENT DOCUMENTS

| | | |
|---|---|---|
| 5,529,785 A | 6/1996 | Dietl |
| 5,559,110 A | 9/1996 | Aungst |
| 5,583,105 A | 12/1996 | Kovacs et al. |
| 5,589,455 A | 12/1996 | Woo |
| 5,603,951 A | 2/1997 | Woo |
| 5,612,301 A | 3/1997 | Inman |
| 5,614,491 A | 3/1997 | Walch et al. |
| 5,635,497 A | 6/1997 | Molenaar |
| 5,637,317 A | 6/1997 | Dietl |
| 5,639,474 A | 6/1997 | Woo |
| 5,639,724 A | 6/1997 | Cavanak |
| 5,645,856 A | 7/1997 | Lacy et al. |
| 5,652,212 A | 7/1997 | Cavanak et al. |
| 5,660,858 A | 8/1997 | Parikh et al. |
| 5,670,478 A | 9/1997 | Stuchlik et al. |
| 5,716,928 A | 2/1998 | Benet et al. |
| 5,741,512 A | 4/1998 | Hauer et al. |
| 5,747,461 A | 5/1998 | Markov |
| 5,756,450 A | 5/1998 | Hahn et al. |
| 5,759,997 A | 6/1998 | Cavanak |
| 5,766,629 A | 6/1998 | Cho et al. |
| 5,807,820 A | 9/1998 | Elias |
| 5,827,822 A | 10/1998 | Floc'h et al. |
| 5,834,017 A | 11/1998 | Cho et al. |
| 5,843,891 A | 12/1998 | Sherman |
| 5,858,401 A * | 1/1999 | Bhalani et al. ............ 424/450 |
| 5,897,876 A | 4/1999 | Rudnic et al. |
| 5,929,030 A | 7/1999 | Hamied et al. |
| 5,932,243 A | 8/1999 | Fricker et al. |
| 5,945,398 A | 8/1999 | Singh et al. |
| 5,952,004 A | 9/1999 | Rudnic et al. |
| 5,958,876 A | 9/1999 | Woo |
| 5,962,019 A | 10/1999 | Cho et al. |
| 5,965,160 A | 10/1999 | Benita et al. |
| 5,980,939 A | 11/1999 | Kim et al. |
| 5,985,321 A | 11/1999 | Brox et al. |
| 5,998,365 A | 12/1999 | Sherman |
| 6,004,580 A | 12/1999 | Backlund et al. |
| 6,008,191 A | 12/1999 | Singh et al. |
| 6,008,228 A | 12/1999 | Bailey et al. |
| 6,022,852 A | 2/2000 | Klokkers et al. |
| 6,028,067 A | 2/2000 | Hong et al. |
| 6,046,163 A | 4/2000 | Stuchlik et al. |
| 6,057,289 A | 5/2000 | Mulye |
| 6,063,762 A | 5/2000 | Hong et al. |
| 6,106,860 A | 8/2000 | Stuchlik et al. |
| 6,136,357 A | 10/2000 | Dietl |
| 6,159,933 A | 12/2000 | Sherman |
| 6,187,747 B1 | 2/2001 | Singh et al. |
| 6,193,985 B1 | 2/2001 | Sonne |
| 6,194,401 B1 | 2/2001 | Salini |
| 6,197,335 B1 | 3/2001 | Sherman |
| 6,204,243 B1 | 3/2001 | Posanski |
| 6,210,712 B1 | 4/2001 | Edgren et al. |
| 6,228,399 B1 | 5/2001 | Parikh et al. |
| 6,239,124 B1 | 5/2001 | Zenke et al. |
| 6,258,808 B1 | 7/2001 | Hauer et al. |
| 6,262,022 B1 | 7/2001 | Hauer et al. |
| 6,267,985 B1 | 7/2001 | Chen et al. |
| 6,280,770 B1 | 8/2001 | Pather et al. |
| 6,284,268 B1 | 9/2001 | Mishra et al. |
| 6,346,511 B1 | 2/2002 | Singh et al. |
| 6,420,355 B2 | 7/2002 | Richter et al. |
| 6,475,519 B1 | 11/2002 | Meinzer et al. |
| 6,696,413 B2 | 2/2004 | Fischer et al. |
| 6,916,785 B2 | 7/2005 | Patel |
| 7,070,802 B1 * | 7/2006 | Bhalani et al. ............ 424/455 |
| 7,153,834 B2 | 12/2006 | Patel |
| 2002/0009067 A1 | 1/2002 | Sachs et al. |
| 2002/0099067 A1 | 7/2002 | Posanski |
| 2004/0048789 A1 | 3/2004 | Patel |

FOREIGN PATENT DOCUMENTS

| | | |
|---|---|---|
| EP | 256856 | 2/1988 |
| EP | 274431 | 7/1988 |
| EP | 760237 | 3/1997 |
| GB | 2015339 | 9/1979 |
| GB | 2222770 | 3/1990 |
| GB | 2228198 | 8/1990 |
| GB | 2257359 | 1/1993 |
| JP | 61-249918 A | 11/1986 |
| JP | 61-280435 A | 12/1986 |
| WO | WO 92/10996 A1 | 7/1992 |
| WO | WO 9221348 | 12/1992 |
| WO | WO 96/36316 | 11/1996 |
| WO | WO 99/44584 | 9/1999 |

OTHER PUBLICATIONS

Cavanak and Sucker, "Formation of Dosage Forms", Prog. Allergy, vol. 38, pp. 65-72, 1986 (Karger, Basel).

Data Sheet for Labrasol, dated 1992, from Gattefossè Corp. (2 pages).

Technical bulletin for Cremophor EL, dated Apr. 1996, from BASF Corp.

Data Sheet for Labrafac Lipophile WL 1349, dated 1992 (2 pages).

Product Information on Capmul MCM C8, dated Oct. 31, 1996, from Abitec Corp.

Cheng et al., "Development of an Azopolymer Based Colonic Release Capsule for Delivering Proteins/Micromolecules," Meth. Find. Exp. Clin. Pharmacol., 1994, 16(4):271-278.

Patel et al., Biological Activity of Insulin in Microemulsion in Mice, J. Pharm. Sci., vol. 80, No. 6, Jun. 1991, 613-614.

Rao et al., "Colonic drug delivery of small peptides," S.T.P. Pharma Sciences 5 (1) 19-29 1995.

Ritschel et al., "Rectal Delivery System for Insulin," Meth. Find. Exp. Clin. Pharmacol., 1988, 10 (10): 645-656.

Ritschel et al., Study on the P.O. Absorption of the Dekapeptide Cyclosporin, Pharm. Res., 5 (10) S-108 (1988).

Ritschel, "Biopharmmaceutic and Pharmacokinetic Aspects in the Design of Controlled Release Peroral Drug Delivery Systems," Drug Dev. And Ind. Pharm., 15 (6 & 7), 1073-1103 (1989).

Ritschel et al., "Study on the Peroral Absorption of the Endekapeptide Cyclosporine A," Meth. Find. Exp. Clin. Pharmacol., 1989, 11 (4): 281-287.

Ritschel, "Gastrointestinal Absorption of Peptides Using Microemulsions as Delivery Systems," B.T. Gattfossè No. 83, 7-22 (1990).

Ritschel et al., "The Site of Absorption in the Gastrointestinal Tract for Insulin from a Microemulsion," Pharm. Res., 7 (9) S-157 (1990).

Ritschel et al., On the Mechanism of Gastrointestinal Absorption of Cyclosporine from a Microemulsion (I)—Site of Absorption, Pharm. Res., 7(9) S-119 (1990).

Ritschel et al., On the Mechanism of Gastrointestinal Absorption of Cyclosporine from a Microemulsion (II)—Effects of Bile Duct Ligation and Pancreatectomy, Pharm. Res., 7(9) S-120 (1990).

Ritschel et al., "Improvement of Peroral Absorption of Cyclosporine A by Microemulsions," Meth. Find. Exp. Clin. Pharmacol. 1990, 12(2): 127-134.

Ritschel, "Targeting in the Gastrointestinal Tract: New Approaches," Meth. Find. Exp. Clin. Pharmacol., 1991, 13(5): 313-336.

Ritschel, "Microemulsions for Improved Peptide Absorption from the Gastrointestinal Tract," Meth. Find. Exp. Clin. Pharmacol., 1991, 13(3): 205-220.

Ritschel et al., Peptide Delivery via Microemulsions, in Progress in Lymphology—XIII, 229-234 (Elsevier Science Publishers 1992).

Ritschel, "Microemulsion technology in the reformation of cyclosporine: the reason behind the pharmacokinetic properties of Neoral," Clin. Transplantation, 1996: 10:364-373.

Shichiri et al., "Increased Intestinal Absorption of Insulin in a Micellar Solution: Water-in-Oil-in-Water Insulin Micelles," Acta Diabet. Lat., 15, 175-183, 1978.

Tarr et al., "Enhanced Intestinal Absorption of Cyclosporine in Rats Through the Reduction of Emulsion Droplet Size," Pharm. Res. vol. 6, No. 1, 1989, 40-43.

Certificate of Analysis on Capmul MCM C8, dated Feb. 6, 1997, from Abitec Corp.

Test Results on dl-x-tocopherol USP, dated Jul. 7, 1997, from Hoffman-LaRoche Inc.

Certificate of Analysis for Captex 300, dated Jun. 25, 1996, from Abitec Corp.

Certificate of Analysis on Capmul MCM, dated Mar. 17, 1997, from Abitec Corp.

Product Information for Capmul MCM, dated Mar. 1994, from Abitec Corp.

Manufacturer's Test Certificate for IMWITOR 308, dated Sep. 1, 1995, from Hüls AG.

Certificate of Analysis on polysorbate 80, dated Jun. 24, 1996, from Spectrum Quality Products, Inc.

English language translation of JP 61-249918 A, cited on Form PTO/SB/08A as document FP1.

English language translation of JP 61-280435 A, cited on Form PTO/SB/08A as document FP2.

* cited by examiner

PHARMACEUTICAL COMPOSITIONS FOR LIPOPHILIC DRUGS

CROSS-REFERENCE TO RELATED APPLICATIONS

This application is a continuation of U.S. patent application Ser. No. 10/207,146, filed Jul. 30, 2002; which is a continuation of U.S. patent application Ser. No. 09/797,912, filed Mar. 5, 2001, now U.S. Pat. No. 7,070,802; which is a continuation of U.S. patent application Ser. No. 09/196,353, filed Nov. 19, 1998, now abandoned (the disclosures of all of which are incorporated by reference herein in their entireties); which is a continuation-in-part of U.S. patent application Ser. No. 08/786,314, filed Jan. 22, 1997, now U.S. Pat. No. 5,858,401; which claims the benefit of U.S. Provisional Patent Application Ser. No. 60/010,410, filed Jan. 22, 1996 (the disclosures of all of which are incorporated by reference herein in their entireties).

BACKGROUND OF THE INVENTION

1. Field of the Invention

The present invention relates to pharmaceutical compositions in the form of self-emulsifying systems. More particularly, the present invention is directed to pharmaceutical compositions, preferably cyclosporin compositions, which form an emulsion in the presence of aqueous media and environments, for example, water and gastrointestinal fluids.

2. Discussion of Background Information

Cyclosporins form a class of polypeptides well known for possessing immunosuppressive and anti-inflammatory activity. The most commonly known cyclosporin is cyclosporin-A, which is commercially available as Sandimmune® and Neoral® in soft gelatin capsule dosage form and as a liquid drink-solution.

Cyclosporins are hydrophobic substances exhibiting poor water solubility and unsatisfactory bioavailability. Oral liquid formulations containing oil, ethanol, and a surfactant such as LABRAFIL®, which is a transesterification product of a triglyceride and a polyol, are disclosed in U.S. Pat. No. 4,388,307. However, these formulations are characterized by a variety of disadvantageous properties, including unpleasant taste, which make these formulations undesirable for long-term therapy. Encapsulation in soft gelatin capsules improves the taste-acceptability of the liquid, but because of the presence of the hydrophilic component (ethanol) in the capsules, they must be packaged in specialized, expensive airtight blister or aluminum foil blister packs. The bioavailability of these liquid and soft gel formulations is low (approximately 30%) and also variable.

U.S. Pat. No. 5,342,625 discloses cyclosporin formulations indicated to have enhanced bioavailability. In addition to cyclosporin, the formulation disclosed in this patent includes a hydrophilic phase, a lipophilic phase, and a surfactant. The hydrophilic phase comprises either 1,2-propylene glycol or an ether of the formula $R_1$—(—O—$(CH_2)_2)_x$—$OR_2$, wherein $R_1$ is alkyl or tetrahydrofurfuryl, $R_2$ is alkyl, tetrahydrofurfuryl, or hydrogen, and X is an integer of 1 to 6. Such ethers are commercially available under the trademarks TRANSCUTOL®, COLYCOFUROL®, and GLYCOFUROL®. The hydrophilic phase may additionally contain $C_{1-5}$ alkanols, such as ethanol. The formulation disclosed in U.S. Pat. No. 5,342,625, therefore, like those of U.S. Pat. No. 4,388,307, requires special packaging, such as aluminum foil blister packs. Further, ethers in the formulations disclosed in U.S. Pat. No. 5,342,625, such as the indicated TRANSCUTOL® and GLYCOFUROL®, are restricted by several regulatory agencies worldwide, including the United States Food and Drug Administration, because these compounds are not considered "generally recognized as safe" (G.R.A.S.) for oral use.

U.S. Pat. No. 5,154,930 discloses lipophilic drug compositions which form suspensions of lipid aggregates when introduced to an aqueous phase and agitated. Illustrations of the invention include compositions of cyclosporin A. The compositions comprise a non-aqueous water-miscible solvent (hydrophilic phase), preferably ethanol or polyethylene glycol. The compositions also require a desalted charged lipid which is soluble in the water-soluble solvent, and which exhibits limited sedimentation upon dispersal in the aqueous medium of suspension formation.

There is a need for improved formulations that can be inexpensively and conventionally packaged, such as in glass or O.H.D. polyethylene bottles. There is also a need for formulations, e.g., oral formulations, whose components comprise only G.R.A.S. excipients.

Alcohol-free pre-emulsion concentrates are known, but also have flaws. For example, the formulation of U.S. Pat. No. 5,206,219 requires a multitude of ingredients, including a protease inhibitor, cholesterol, a phospholipid, a surfactant, a polyol, and a lipid solvent.

U.S. Pat. No. 4,990,337 discloses solutions of cyclosporin in monoglycerides or diglycerides of $C_6$ to $C_{10}$ fatty acids, preferably in a $C_8$ diglyceride, which can be emulsified in water. All of the examples describe preparing emulsions by making two solutions—one containing cyclosporin and a fatty acid glyceride, and the other containing water with a small amount of surfactant—mixing the solutions, and emulsifying them with laboratory equipment. Although Test Example 2 discloses that capric acid monoglyceride, when shaken with water, would emulsify in a manner "very close to self-emulsification," there is no teaching or suggestion of how to prepare a cyclosporin composition which forms a fine emulsion on contact with an aqueous phase.

U.S. Pat. No. 5,759,997, discloses compositions comprising cyclosporin, a mixture of mono-, di-, and triglycerides, and a hydrophilic tenside. In one embodiment, the mixture of mono-, di-, and triglycerides comes from a single product, such as MAISINE®, whose fatty acid component is mainly long chain. There is no suggestion that these compositions would self-emulsify, nor is there any discussion of how to prepare a cyclosporin composition which forms a fine emulsion on contact with an aqueous phase.

SUMMARY OF THE INVENTION

Lipophilic drug compositions, e.g., cyclosporin compositions, have been discovered which unexpectedly, completely and reliably self-emulsify upon contact with an aqueous phase, such as water or gastrointestinal fluid. In particular, it has been found that lipophilic drugs, such as cyclosporin, exhibit superior self-emulsification ability when dissolved in certain polar lipids, and mixed with a sufficient amount of at least one surfactant.

The present invention is generally described as a "Polar Lipid Self-Emulsifying Drug Delivery System," or PLSEDDS. In the present invention, a novel pharmaceutical formulation for lipophilic drugs, such as cyclosporin, is provided in the form of a PLSEDDS which overcomes problems associated with prior art formulations. The ready-to-use PLSEDDS of the instant invention comprises a lipophilic drug, such as cyclosporin, which is dissolved in a polar lipid and mixed with sufficient surfactant, such that upon contact with an aqueous medium, the composition completely forms a fine emulsion of mean particle size of less than about 50 nm, preferably less than about 30 nm, with a preferred range being from about 15 nm to 30 nm.

PLSEDDS compositions confer several desirable attributes to cyclosporin formulations. For example, the PLSEDDS formulations described herein (i) instantly or spontaneously form fine emulsions on exposure to water or gastrointestinal fluid without the need for specialized equipment, (ii) do not require a hydrophilic cosolvent, and (iii) do not need air tight aluminum blister packaging or other specialized expensive packaging, and (iv) are shelf-stable.

In one aspect, the present invention is directed to a shelf-stable pharmaceutical solution comprising at least one lipophilic drug; a surfactant component; and a polar lipid component, which solution, on contact with an aqueous phase, is capable of spontaneously forming a fine emulsion.

Still further the present invention is directed to a shelf-stable pharmaceutical solution comprising at least one cyclosporin; a surfactant component; and a polar lipid component, wherein the at least one cyclosporin, the surfactant component, and the polar lipid component are present in effective amounts so that the composition, on contact with an aqueous phase, is capable of spontaneously forming a fine emulsion.

Further aspects of the invention, including discussion of specific and preferred components of the solution, such as the lipophilic drug, the surfactant component, the polar lipid component and the inclusion of additional components, such as triglyceride, as well as various forms for administration, are discussed further herein.

DETAILED DESCRIPTION OF THE INVENTION

Unless otherwise indicated, all percentages, parts, ratios, etc. stated herein are by weight. Moreover, all percent values in this application, unless otherwise stated, are calculated by weight based upon 100% of a given sample weight. Thus, for example, 30% represents 30 weight parts out of every 100 weight parts of the sample.

Unless otherwise stated, a reference to a compound or component, includes the compound or component by itself, as well as in combination with other compounds or components, such as mixtures of compounds.

The PLSEDDS compositions of the present invention form fine emulsions on contact with an aqueous phase, such as water or gastrointestinal fluids. The compositions comprise (i) at least one lipophilic drug, (ii) a polar lipid component, and (iii) a surfactant component. The compositions may further include (iv) a triglyceride component.

In particular, it has been found that when cyclosporin is dissolved in certain polar lipids, the presence of a sufficient amount of at least one surfactant in the cyclosporin solution obviates the need for a hydrophilic component, such as disclosed in U.S. Pat. No. 5,342,625. In the composition of the invention, there is therefore no need for a distinct hydrophilic phase. In other words, the composition of the present invention is a solution and therefore does not contain distinct hydrophilic and lipophilic phases.

On exposure to an aqueous medium, such as water or gastrointestinal fluid, the composition of the present invention instantly or spontaneously forms a fine emulsion. A fine emulsion preferably has a mean particle size, e.g., diameter, of less than about 50 nm, even more preferably less than about 30 nm, with a preferred range being from about 15 nm to 30 nm, when measured by photon correlation spectroscopy (PCS) with the particle size being determined using equipment such as a Malvern Zetasizer 1000 (Malvern Instruments Limited, Malvern, UK). Moreover, because no emulsification equipment is required, the formation of the emulsion on contact with an aqueous phase is referred to as self-emulsification. While no agitation and/or emulsification equipment is required to obtain emulsification, agitation and/or emulsification equipment can be utilized.

As discussed herein, lipophilic drugs comprise those drugs which are soluble in polar lipids. These drugs include, but are not limited to, cyclosporins, e.g., cyclosporin A; growth hormones; protease inhibitors; angiotensin-converting enzyme (ACE) inhibitors; cis- and trans-retinoids and their derivatives; parathyroid hormones and hormone analogs; and insulins. Also included are other water-insoluble peptides and proteins such as water-insoluble peptides having a molecular weight of about 400 to about 3,000; and water-insoluble proteins having molecular weights above about 3,000.

Preferably, the lipophilic drugs are polypeptide lipophilic drugs, especially monocyclic polypeptides, in particular the cyclic undecapeptides which form the class of drugs known as the cyclosporins. As discussed herein, the terms cyclosporin and cyclosporins refer to any of the several cyclosporins, and to any two or more of the several cyclosporins, such as in a mixture. In addition to the preferred cyclosporin, cyclosporin-A, other naturally occurring cyclosporin analogs include cyclosporins-B, -C, -D, -E, -F, -G, and so on. Also included are non-naturally occurring cyclosporins, including dihydrocyclosporins, such as dihydrocyclosporin-C and -D; isocyclosporins, such as isocyclosporin-D; other cyclosporin derivatives; and synthetically prepared cyclosporin analogs. The cyclosporin most commonly used is cyclosporin-A, and is commercially available as a mixture which also contains smaller amounts of other cyclosporin analogs.

The lipophilic drug, e.g., cyclosporin, such as cyclosporin-A, may comprise about 5 to 20 wt. %, more preferably about 7 to 14 wt. %, and still more preferably about 7 to 10 wt. % of the composition. Two particularly preferred embodiments comprise about 8 wt. % or about 10 wt. % cyclosporin.

The polar lipid component, as discussed herein, comprises one or more partial glycerides, preferably including one or more fatty acid partial glycerides. Fatty acid partial glycerides, as discussed herein, are monoglycerides and diglycerides. Suitable monoglycerides include α-monoglycerides and β-monoglycerides. Suitable diglycerides include α,α'-diglycerides and α,β-diglycerides, wherein the fatty acid residues may be the same or different.

Preferable polar lipid components, therefore, include polar lipid components which comprise one or more partial glycerides, more preferably one or more fatty acid partial glycerides, e.g., one or more monoglycerides and/or one or more diglycerides—particularly, one or more monoglycerides and/or one or more diglycerides of at least one fatty acid. Monoglycerides and diglycerides of $C_6$-$C_{12}$ fatty acids are preferred, more preferably $C_8$-$C_{10}$ fatty acids. Preferable polar lipid components comprise at least about 45 wt. %, such as at least about 50 wt. %, at least about 55 wt. %, and about 60 wt. % monoglyceride of at least one $C_6$-$C_{12}$ fatty acid, more preferably at least one $C_8$-$C_{10}$ fatty acid. In one preferred embodiment, the polar lipid component comprises $C_6$-$C_{12}$ fatty acid mono- and di-glycerides comprising from about 55 wt. % to 65 wt. % of the polar lipid component.

Preferably, the fatty acid component comprises at least about 80 wt. %, more preferably at least about 90 wt. %, even more preferably at least about 95 wt. %, and even more preferably at least about 99 wt. % of $C_8$ fatty acids, such as caprylic acid, by weight of the fatty acid in the polar lipid component. Of these compositions, particularly preferred are those where the remainder of the fatty acid component consists of, or consists essentially of, or comprises, a $C_{10}$ fatty acid, such as capric acid, whereby the fatty acid chains preferably consist of, or consist essentially of, or comprise, $C_8$ fatty acid, such caprylic acid, and, $C_{10}$ fatty acid, such as capric acid.

Suitable products useful as polar lipid components are marketed by Abitec Corporation of Janesville, Wisc. under the trademarks CAPMUL® MCM and CAPMUL® MCM $C_8$. Particularly, CAPMUL® MCM as disclosed in the Abitec Group Product Information Sheet entitled "CAPMUL® MCM," Issue: 3, Date: March 1994, and in the Abitec Corporation Mar. 17, 1997 "Certificate of Analysis" for CAPMUL® MCM; Lot No.: 60502-6, and CAPMUL® MCM $C_8$ as disclosed in the Abitec Group Product Information Sheet entitled "CAPMUL MCM $C_8$ CAS #26402-22-2," Issue: 2, Date: Oct. 31, 1996, and in the Abitec Corporation Feb. 6, 1997 "Certificate of Analysis" for CAPMUL® MCM (C8); Lot No.: 60114-8, may be used. These Product Information Sheets and Certificates of Analysis are hereby incorporated herein in their entireties by reference thereto.

The polar lipid component may comprise from about 5 wt. % to 50 wt. %, more preferably from about 20 wt. % to 50 wt. %, and even more preferably about 30 wt. % to 45 wt. % of the composition of the invention.

The surfactant component of the invention may include one or more surfactants. While various surfactants can be utilized, nonionic surfactants, particularly hydrophilic nonionic surfactants, are preferred. The surfactant component preferably has an HLB (hydrophilic-lipophilic balance) of from about 10 to 16, and more preferably from about 12 to 14. Where the surfactant component includes two or more surfactants, each or any surfactant in the surfactant component preferably has an HLB of about from 10 to 16, and more preferably from about 12 to 14.

Among the surfactants which may be used are the reaction products of natural or hydrogenated vegetable oils and ethylene oxide, as disclosed in U.S. Pat. No. 5,342,625, which is hereby incorporated herein in its entirety by reference thereto. These include polyoxyethylated natural vegetable oils, such as polyoxyethylated natural castor oils, and polyoxyethylated hydrogenated vegetable oils, such as polyoxyethylated hydrogenated castor oils. In accordance with the foregoing, polyoxyethylene glycerol triricinoleate, PEG(35) natural castor oil, PEG(35) hydrogenated castor oil, PEG(40) natural castor oil, and PEG(40) hydrogenated castor oil may be used.

Appropriate commercially available surfactants include CREMOPHOR® RH40, a PEG(40) hydrogenated castor oil, and CREMOPHOR® EL, a PEG(35) natural castor oil, these being sold by BASF Corporation of Midland, Mich. Particularly, CREMOPHOR® EL, as disclosed in the BASF April 1996 Technical Bulletin entitled "CREMOPHOR EL; CTFA/INCI: PEG-35 Castor Oil," is preferred for the surfactant component. This Technical Bulletin is hereby incorporated herein in its entirety by reference thereto.

Another useful class of surfactants comprise polyglycolyzed glycerides or ethoxylated glycerides having a molecular weight of PEG from about 400 to about 2,000 and a fatty acid chain length of from six to eighteen carbon atoms; particularly, polyglycolyzed $C_8$-$C_{10}$ glycerides, and most especially saturated polyglycolyzed $C_8$-$C_{10}$ glycerides, are suitable. Examples of substances that may be used include PEG (8) caprylic-capric glyceride, e.g., LABRASOL®, sold by Gattefosse Corporation of Lyon, France. LABRASOL is characterized in the Gattefosse IV/92/2 two page Data Sheet entitled "LABRASOL," which is hereby incorporated herein in its entirety by reference thereto.

Other surfactants that may be used include polyoxyethylene sorbitan esters, i.e., lauryl, palmityl, stearyl, oleyl and trioleyl esters of polyoxyethylene sorbitan, which are commercially available as TWEEN® 20 (polysorbate 20), TWEEN® 40 (polysorbate 40), TWEEN® 60 (polysorbate 60), TWEEN® 80 (polysorbate 80) and TWEEN® 85 (polysorbate 85), respectively.

A particularly suitable combination of surfactants comprises a polyoxyethylated natural or hydrogenated castor oil, such as PEG(3 5) natural castor oil, PEG(40) hydrogenated castor oil, and CREMOPHOR® EL, with CREMOPHOR® EL being preferred, as a first surfactant, and a polyglycolyzed $C_8$-$C_{10}$ glyceride, preferably LABRASOL®, as a second surfactant. The composition preferably comprises from about 50 to 60 wt. % of the first and second surfactants. A weight ratio of first surfactant to second surfactant of from about 1:1 to 20:1, preferably about 1:1 to 9:1, more preferably 3:1 to 9:1, and most preferably from about 5:1 to 9:1, is especially preferred.

The surfactant component may comprise from about 30 to 75 wt. %, preferably about 45 to 60 wt. % by weight of the composition. Particular embodiments include about 50 wt. %, 56 wt. %, 67 wt. %, 63 wt. % or 73 wt. % surfactant by weight.

Although the above specifically recited surfactants, mixtures, and concentrations are preferable, any surfactant or mixture of surfactants, at any concentration, can be utilized that enables self-emulsification of the composition when the composition is added to an aqueous medium.

The composition of the invention can further include a triglyceride component. The triglyceride component can comprise one or more triglyceride compositions—particularly, one or more triglycerides of at least one fatty acid, preferably $C_6$-$C_{12}$ fatty acid, more preferably $C_6$-$C_{10}$ fatty acid. The fatty acid triglycerides as disclosed in U.S. Pat. No. 5,342,625, which is incorporated by reference in its entirety, may be employed.

A commercially available triglyceride composition that may be used is LABRAFAC LIPOPHILE WL 1349, available from Gattefosse Corporation, Lyon, France. Particularly, this composition as disclosed in the IV/92/II two page Data Sheet entitled "LABRAFAC LIPOPHILE WL 1349" is appropriate for the triglyceride component. This Data Sheet is hereby incorporated herein in its entirety by reference thereto.

When present, the triglyceride component preferably comprises about 10 wt. % or less of the composition, more preferably less than about 5 wt. %, with a preferred range being about 1 to 5 wt. %, more preferably about 2 to 4 wt. %, of the composition of the invention. Particular embodiments comprise about 2.5 wt. % or about 10 wt. % triglyceride component.

The composition of the invention may further contain additives, for example, sweetening agents, and/or stabilizers such as one or more antioxidants and/or preservatives. Vitamin E (dl-α-tocopherol) is a preferred antioxidant. A commercial Vitamin E composition that maybe used is available from Hoffmann-La Roche Inc. of Belvedere, N.J. The composition as disclosed in the Jul. 7, 1997 Hoffmann-La Roche Inc. Quality Control Department sheet, entitled "605250003 DL-AL-TOCOPH-USP/FCC", is suitable. This sheet is hereby incorporated herein in its entirety by reference thereto.

An advantage of the compositions of the present invention is shelf stability, which preferably includes both chemical and physical stability. Chemical stability includes stability of the composition against chemical degradation, e.g., hydrolysis, oxidation/reduction, photolysis, etc. Physical stability refers to stability against change in physical form, including, e.g., no, or essentially no, crystallization of the active ingredient from the solution. Compositions are preferably shelf-stable for at least the interval from when the composition is manufactured to the time when the patient could reasonably be expected to take the composition. Compositions are also preferably shelf-stable when subjected to typical manufacturing and marketing conditions, such as storage and transportation. Compositions of the present invention are preferably shelf-stable for at least three months under accelerated challenge conditions (40° C. and 75% relative humidity) and for at least two years under recommended storage conditions, such as ambient temperature.

Compositions examined without a polar lipid component, such as a $C_6$-$C_{12}$ monoglyceride, are not shelf-stable, as evidenced by crystallization on storage at room temperature for as little as one day. This shelf-instability renders them unsuitable for practical use. Cyclosporin formulations of the present invention, containing a polar lipid component, were shelf-stable for at least three months, and did not undergo crystallization of cyclosporin under accelerated challenge storage conditions.

PLSEDDS compositions of the present invention, therefore, include compositions comprising a lipophilic drug, a polar lipid component, and a surfactant component and optionally a triglyceride component having the ability to form fine emulsion upon contact with an aqueous environment, and preferably in the proportions, described above. In this regard, as will be recognized by those of ordinary skill in the art, the present invention is not limited to the disclosed proportions of ingredients. Any composition, preferably shelf-stable, having proportions of lipophilic drug, polar lipid, surfactant, and (optionally) triglyceride, which is capable of instantly or spontaneously forming an emulsion on contact with an aqueous phase is within the scope of the present invention.

Thus, one particular composition of the present invention can comprise from about 7 to 14 wt. % cyclosporin, from about 30 to 50 wt. % polar lipid component (preferably partial glycerides of $C_6$-$C_{12}$ fatty acids), from about 40 to 60 wt. % surfactant component, and optionally, from about 2% to 4 wt. % triglyceride component.

Another preferred composition comprises from about 7 to 10 wt. % cyclosporin; from about 30 to 45 wt. % polar lipid component, wherein the polar lipid component comprises at least 45 wt. % monoglyceride of $C_6$-$C_{12}$ fatty acids; from about 45 to 60 wt. % surfactant component; and optionally, from about 2 wt. % to about 4 wt. % triglyceride component.

Still another especially preferred composition comprises from about 7 to 10 wt. % cyclosporin A; from about 30 to 45 wt. % polar lipid component, wherein the polar lipid component comprises about 60 wt. % monoglyceride of caprylic and capric acids; about 50 to 60 wt. % surfactant component, wherein the surfactant component comprises a first surfactant comprising a polyoxyethylated castor oil, preferably a PEG (35) natural castor oil, and a second surfactant comprising a saturated polyglycolyzed $C_8$-$C_{10}$ glyceride, preferably in a weight ratio of first surfactant to second surfactant of from about 5:1 to about 9:1; and from about 2 to 4 wt. % triglyceride component.

Still another especially preferred composition comprises from about 7 to 10 wt. % cyclosporin A; from about 30 to 45 wt. % polar lipid component comprising about 60 wt. % monoglycerides of caprylic and capric acids; and from about 45 to 60 wt. % surfactant component, wherein the surfactant component comprises a polyoxyethylated castor oil, preferably a PEG(35) natural castor oil.

Still another preferred composition comprises from about 7 to 10 wt. % cyclosporin A; from about 20 to 30 wt. % polar lipid component comprising about 60 wt. % monoglycerides of caprylic and capric acids; and about 60 to 70 wt. % surfactant component, wherein the surfactant component comprises a polyoxyethylated castor oil, preferably a PEG(40) hydrogenated castor oil.

Still another preferred composition comprises from about 7 to 10 wt. % cyclosporin A; from about 5 to 10 wt. % polar lipid component comprising about 60% monoglycerides of caprylic and capric acids; from about 65 to 80 wt. % surfactant component, wherein the surfactant component comprises a mixture of polyoxyethylated castor oil, preferably a PEG (40) hydrogenated castor oil, and polyglycolyzed or ethoxylated glycerides, in a weight ratio of from about 1:1 to 3:1; and less than about 10 wt. % of a triglyceride component.

The following examples provide additional information on some of the compositions of the present invention. It should be understood that these examples are not meant to constitute a comprehensive list of the scope of the invention. Other compositions within the scope of the invention can be prepared, as will be understood by those of ordinary skill in the art.

EXAMPLE 1

Cyclosporin-A (1.0 g) was dissolved in Capmul® MCM (5.0 g) at 25° C. to 30° C. Tween 80 (6.0 g) was added and then mixed to achieve a homogeneous solution. The mixture appeared as a clear solution to the naked eye, and a microscopic analysis revealed no crystals. An amount of the solution, such that each capsule contained 50 mg of cyclosporin, was filled into soft gelatin capsules.

EXAMPLE 2

Cyclosporin (1.0 g) was dissolved in Capmul® (MCM) (2.3 g) at 25° C. to 30° C. LABRASOL® (4.5 g) and PEG-400 (0.76 g) were added and mixed to achieve a homogenous solution. The mixture appeared as a clear solution to the naked eye, and a microscopic analysis revealed no crystals. An amount of the solution, such that each capsule contained 100 mg of cyclosporin, was filled into soft gelatin capsules.

EXAMPLES 3-5

The remaining examples were made according to the above procedure. The quantities are listed in the following table in grams:

| Ingredients | Example 3 | Example 4 | Example 5 |
|---|---|---|---|
| Cyclosporin | 0.50 | 0.50 | 0.50 |
| CAPMUL ® MCM | 2.50 | 2.00 | 2.00 |
| LABRASOL ® | — | 1.26 | 1.26 |
| TWEEN 80 | 2.50 | 1.28 | — |
| TWEEN 20 | — | — | 1.28 |
| Total | 5.50 | 5.04 | 5.04 |

In each case, the mixture appeared as a clear solution to the naked eye, and a microscopic analysis revealed no crystals.

An amount of the solution, such that each capsule contained 50 mg of cyclosporin, was filled into soft gelatin capsules.

EXAMPLE 6

Capmul® MCM $C_8$ (9.0000 kg) was added to a 40 L pot and melted to a homogenous liquid at 40° C. to 50° C. The Capmul® MCM $C_8$ was stirred thoroughly with a pneumatic air stirrer at a setting of #20, with nitrogen purge. Cremophor® EL (13.4865 kg), LABRASOL® (1.5750 kg), LABRAFAC LIPOPHILE WL 1349 (0.6750 kg) and vitamin E (0.0135 kg) were added to the pot and the contents of the pot were mixed for 15 minutes. The liquid was then cooled to ambient temperature (20° C.-30° C.) without stirring. The stirrer was restarted at a slow speed and the cyclosporin (2.2500 kg) was slowly added to the pot. The stirrer speed was gradually increased so that the cyclosporin powder was folded into the liquid at the minimal vortex formed by the mixer action. Mixing was continued until the cyclosporin powder was completely dissolved and the liquid appeared clear. Microscopic analysis revealed no crystals. The solution was vacuum deaerated no more than 4 hours prior to encapsulation. The composition was used to fill 90,000 soft gelatin capsules each containing 25 mg of cyclosporin.

EXAMPLE 7

A batch of 22,500 soft gelatin capsules each containing 100 mg of cyclosporin was prepared according to the procedure described in Example 6, utilizing the following quantities:

| Ingredients | Quantity Added (kg) | mg/unit |
| --- | --- | --- |
| Cyclosporin-A USP | 2.2500 | 100.00 |
| Capmul ® MCM $C_8$ | 9.0000 | 400.00 |
| Cremophor ® EL | 13.4865 | 599.40 |
| LABRASOL ® | 1.5750 | 70.00 |
| LABRAFAC LIPOPHILE WL | 0.6750 | 30.00 |
| Vitamin E | 0.0135 | 0.60 |

The solution appeared clear by visual examination, and a microscopic analysis revealed no crystals. An amount of the solution, such that each capsule contained 100 mg of cyclosporin, was used to fill 22,500 soft gelatin capsules.

EXAMPLE 8

Capmul® MCM $C_8$ (416.67 mg) was melted to a homogenous liquid at about 40° C. to 50° C. Cremophor® EL (500 mg) and vitamin E (0.25 mg) were added to the melted Capmul® MCM $C_8$ and the mixture was stirred for 15 minutes. Cyclosporin (83.33 mg) was added and mixing continued until the cyclosporin was completely dissolved. The solution, which appeared clear by visual examination, was used to fill soft gelatin capsules. No crystals were revealed by a microscopic analysis.

EXAMPLE 9

A batch of 10 soft gelatin capsules, each containing 100 mg of cyclosporin, was prepared according to the procedure described in Example 8. Because of the smaller scale of the batch, the ingredients were mixed with a magnetic stirrer in a beaker. The following ingredients, in the listed amounts, were utilized:

| Ingredients | Quantity (g) | mg/unit |
| --- | --- | --- |
| Cyclosporin-A USP | 1.00 | 100.00 |
| CAPMUL ® MCM $C_8$ | 3.00 | 300.00 |
| CREMOPHOR ® RH40 | 8.00 | 800.00 |
| Total | 12.00 | 1200.00 |

The resulting solution was clear by visual examination.

EXAMPLE 10

A batch of 10 soft gelatin capsules, each containing 100 mg of cyclosporin, was prepared according to the procedure described in Example 8. Because of the smaller scale of the batch, the ingredients were mixed with a magnetic stirrer in a beaker. The following ingredients, in the listed amounts, were utilized:

| Ingredients | Quantity (g) | mg/unit |
| --- | --- | --- |
| Cyclosporin-A USP | 1.00 | 100.00 |
| CAPMUL ® MCM $C_8$ | 1.00 | 100.00 |
| CREMOPHOR ® RH40 | 6.00 | 600.00 |
| LABRAFAC ® CM10* | 4.00 | 400.00 |
| Total | 12.00 | 1200.00 |

*LABRAFAC ® CM10 is a commercially available mixture of 70 wt. % LABRASOL ® and 30 wt. % LABRAFAC ® LIPOPHILE, sold by Gattefosse Corporation of Lyon, France.

The resulting solution was clear by visual examination.

COMPARATIVE EXAMPLES 1-5

Five cyclosporin formulations were prepared without a polar lipid component according to the following table. All quantities are listed in grams.

| Ingredients | Comparative Example 1 | Comparative Example 2 | Comparative Example 3 | Comparative Example 4 | Comparative Example 5 |
| --- | --- | --- | --- | --- | --- |
| Cyclosporin | 1.00 | 0.50 | 1.00 | 1.00 | 0.50 |
| LABRASOL ® | 5.04 | 2.50 | 2.50 | 9.01 | 2.52 |
| PEG-400 | 2.55 | 1.52 | 5.51 | 1.10 | — |
| Corn Oil | — | — | — | — | 2.51 |
| Total | 8.59 | 4.52 | 9.01 | 11.11 | 5.53 |

Each of the compositions of Comparative Examples 1-5, was a hazy liquid. Microscopic analysis revealed the presence of undissolved crystals in all five of the mixtures.

Compositions of the present invention may be used as liquids for oral administration or encapsulated, for example, in soft or hard gelatin shells or capsules. The following is a gel formulation that can be employed.

| Ingredients | Amounts (kg) |
| --- | --- |
| Gelatin NF | 45.500 |
| Glycerin USP | 7.830 |
| Purified Water | 28.500 |
| Sorbitol Special 76% | 14.500 |
| Titanium Mass | 5.506 |

Finally, although the invention has been described with reference to particular means, materials, and embodiments, it should be noted that the invention is not limited to the particulars disclosed, and extends to all equivalents within the scope of the claims.

The invention claimed is:

1. A pharmaceutical composition comprising:
   a) at least one cyclosporin;
   b) a surfactant comprising polyoxyethylated castor oil and saturated polyglycolyzed $C_8$-$C_{10}$ glycerides; and
   c) a polar lipid component comprising at least one fatty acid partial glyceride comprising at least 50 weight percent monoglycerides of $C_6$-$C_{12}$ fatty acids; and
   d) said pharmaceutical composition does not contain a hydrophilic phase containing 1,2-propylene glycol or an ether of formula $R_1$—(—O—$(CH_2)_2)_x$—$OR_2$, wherein $R_1$ is alkyl or tetrahydrofurfuryl, $R_2$ is alkyl, tetrahydrofurfuryl, or hydrogen, and x is an integer of 1 to 6; and
   wherein said at least one cyclosporin, said surfactant component, and said polar lipid component are present in effective amounts relative to each other so that the composition, on contact with an aqueous phase, is capable of spontaneously forming a fine emulsion, wherein the weight ratio of said polyoxyethylated castor oil to said saturated polyglycolyzed $C_8$-$C_{10}$ glycerides is from about 1:1 to 20:1.

2. The pharmaceutical composition according to claim 1, wherein the weight ratio of said polyoxyethylated castor oil to said saturated polyglycolyzed $C_8$-$C_{10}$ glycerides is from about 5:1 to 9:1.

3. A shelf-stable pharmaceutical composition comprising:
   a) at least one cyclosporin;
   b) a surfactant component comprising polyoxyethylated castor oil and saturated polyglycolyzed $C_8$-$C_{10}$ glycerides;
   c) a polar lipid component; and
   d) said pharmaceutical composition does not contain a hydrophilic phase containing 1,2-propylene glycol or an ether of formula $R_1$—(—O—$(CH_2)_2)_x$—$OR_2$, wherein $R_1$ is alkyl or tetrahydrofurfuryl, $R_2$ is alkyl, tetrahydrofurfuryl, or hydrogen, and x is an integer of 1 to 6; and
   wherein said at least one cyclosporin, said surfactant component, and said polar lipid component are present in effective amounts relative to each other so that the composition, on contact with an aqueous phase, is capable of spontaneously forming a fine emulsion, wherein the weight ratio of said polyoxyethylated castor oil to said saturated polyglycolyzed $C_8$-$C_{10}$ glycerides is from about 1:1 to 20:1.

4. The pharmaceutical composition according to claim 3, wherein the weight ratio of said polyoxyethylated castor oil to said saturated polyglycolyzed $C_8$-$C_{10}$ glycerides is from about 5:1 to 9:1.

5. A pharmaceutical composition comprising:
   a) at least one cyclosporin;
   b) a surfactant comprising polyoxyethylated castor oil and saturated polyglycolyzed $C_8$-$C_{10}$ glycerides;
   c) a polar lipid component comprising at least one fatty acid partial glyceride comprising at least 50 weight percent monoglycerides of $C_6$-$C_{12}$ fatty acids;
   d) at least one triglyceride; and
   wherein said pharmaceutical composition does not contain a hydrophilic phase containing 1,2-propylene glycol or an ether of formula $R_1$—(—O—$(CH_2)_2)_x$—$OR_2$, wherein $R_1$ is alkyl or tetrahydrofurfuryl, $R_2$ is alkyl, tetrahydrofurfuryl, or hydrogen, and x is an integer of 1 to 6; and
   wherein said at least one cyclosporin, said surfactant component, and said polar lipid component are present in effective amounts relative to each other so that the composition, on contact with an aqueous phase, is capable of spontaneously forming a fine emulsion, wherein the weight ratio of said polyoxyethylated castor oil to said saturated polyglycolyzed $C_8$-$C_{10}$ glycerides is from about 1:1 to 20:1.

6. A pharmaceutical composition comprising:
   a) about 5 to 20 weight percent of at least one cyclosporin;
   b) about 30 to 75 weight percent of a surfactant component comprising a polyoxyethylated castor oil;
   c) about 5 to 50 weight percent of a polar lipid component comprising at least one fatty acid partial glyceride comprising at least 50 weight percent monoglycerides of $C_6$-$C_{12}$ fatty acids;
   d) at least one fatty acid triglyceride in an amount not more than about 10 weight percent;
   wherein said pharmaceutical composition does not contain a hydrophilic phase containing 1,2-propylene glycol or an ether of formula $R_1$—(—O—$(CH_2)_2)_x$—$OR_2$, wherein $R_1$ is alkyl or tetrahydrofurfuryl, $R_2$ is alkyl, tetrahydrofurfuryl, or hydrogen, and x is an integer of 1 to 6;
   wherein said at least one cyclosporin, said surfactant component, and said polar lipid component are present in effective amounts relative to each other so that the composition, on contact with an aqueous phase, is capable of spontaneously forming a fine emulsion,
   wherein said surfactant further comprises a saturated polyglycolyzed $C_8$-$C_{10}$ glycerides, and wherein the weight ratio of polyoxyethylated castor oil to saturated polyglycolyzed $C_8$-$C_{10}$ glycerides is about 5:1 to 9:1.

7. A shelf-stable pharmaceutical composition comprising:
   a) at least one cyclosporin;
   b) a surfactant component comprising polyoxyethylated castor oil and saturated polyglycolyzed $C_8$-$C_{10}$ glycerides;
   c) a polar lipid component;
   d) a triglyceride component, which is present in an amount not more than about 10 weight percent; and
   wherein said pharmaceutical composition does not contain a hydrophilic phase containing 1,2-propylene glycol or an ether of formula $R_1$—(—O—$(CH_2)_2)_x$—$OR_2$, wherein $R_1$ is alkyl or tetrahydrofurfuryl, $R_2$ is alkyl, tetrahydrofurfuryl, or hydrogen, and x is an integer of 1 to 6; and
   wherein said at least one cyclosporin, said surfactant component, and said polar lipid component are present in effective amounts relative to each other so that the composition, on contact with an aqueous phase, is capable of spontaneously forming a fine emulsion, wherein the weight ratio of said polyoxyethylated castor oil to said saturated polyglycolyzed $C_8$-$C_{10}$ glycerides is from about 1:1 to 20:1.

8. The pharmaceutical composition according to claim 1, wherein the pharmaceutical composition does not contain a hydrophilic component.

9. The pharmaceutical composition according to claim 1, wherein the pharmaceutical composition does not contain distinct hydrophilic and lipophilic phases.

10. The pharmaceutical composition according to claim 2, wherein the pharmaceutical composition does not contain a hydrophilic component.

11. The pharmaceutical composition according to claim 2, wherein the pharmaceutical composition does not contain distinct hydrophilic and lipophilic phases.

12. The pharmaceutical composition according to claim 3, wherein the pharmaceutical composition does not contain a hydrophilic component.

13. The pharmaceutical composition according to claim 3, wherein the pharmaceutical composition does not contain distinct hydrophilic and lipophilic phases.

14. The pharmaceutical composition according to claim 4, wherein the pharmaceutical composition does not contain a hydrophilic component.

15. The pharmaceutical composition according to claim 4, wherein the pharmaceutical composition does not contain distinct hydrophilic and lipophilic phases.

16. The pharmaceutical composition according to claim 5, wherein the pharmaceutical composition does not contain a hydrophilic component.

17. The pharmaceutical composition according to claim 5, wherein the pharmaceutical composition does not contain distinct hydrophilic and lipophilic phases.

18. The pharmaceutical composition according to claim 6, wherein the pharmaceutical composition does not contain a hydrophilic component.

19. The pharmaceutical composition according to claim 6, wherein the pharmaceutical composition does not contain distinct hydrophilic and lipophilic phases.

20. The pharmaceutical composition according to claim 7, wherein the pharmaceutical composition does not contain a hydrophilic component.

21. The pharmaceutical composition according to claim 7, wherein the pharmaceutical composition does not contain distinct hydrophilic and lipophilic phases.

* * * * *